US008273343B2

(12) United States Patent
Lin

(10) Patent No.: US 8,273,343 B2
(45) Date of Patent: *Sep. 25, 2012

(54) PROTEIN-POLYMER CONJUGATES

(75) Inventor: Ko-Chung Lin, Lexington, MA (US)

(73) Assignee: PharmaEssentia Corp., Taipei (TW)

( * ) Notice: Subject to any disclaimer, the term of this patent is extended or adjusted under 35 U.S.C. 154(b) by 14 days.

This patent is subject to a terminal disclaimer.

(21) Appl. No.: 12/533,147

(22) Filed: Jul. 31, 2009

(65) Prior Publication Data

US 2010/0029907 A1 Feb. 4, 2010

Related U.S. Application Data

(60) Provisional application No. 61/085,072, filed on Jul. 31, 2008.

(51) Int. Cl.
*A61K 38/21* (2006.01)
*A61K 38/27* (2006.01)
*A61K 38/19* (2006.01)
*C07K 14/565* (2006.01)
*C07K 14/61* (2006.01)
*C07K 14/505* (2006.01)

(52) U.S. Cl. ........ 424/85.6; 530/351; 514/1.1; 514/7.7; 514/11.3; 424/195.11; 424/193.1; 424/198.1

(58) Field of Classification Search ............... None
See application file for complete search history.

(56) References Cited

U.S. PATENT DOCUMENTS

| 5,643,575 | A | 7/1997 | Martinez |
| 5,824,784 | A | 10/1998 | Kinstler |
| 5,919,455 | A | 7/1999 | Greenwald |
| 5,932,462 | A | 8/1999 | Harris |
| 5,951,974 | A | 9/1999 | Gilbert |
| 5,985,265 | A | 11/1999 | Kinstler |
| 7,090,835 | B2 | 8/2006 | Gabriel |
| 7,157,546 | B2 | 1/2007 | Kozlowski |
| 2005/0009988 | A1 | 1/2005 | Harris |
| 2005/0107277 | A1 | 5/2005 | Lin et al. |
| 2005/0143292 | A1 | 6/2005 | DeFrees et al. |

FOREIGN PATENT DOCUMENTS

| WO | 2004/022630 | | 3/2004 |
| WO | 2006/024953 | | 3/2006 |
| WO | WO2006/095029 | * | 9/2006 |

OTHER PUBLICATIONS

Dictionary.com definition of "moiety", Dec. 3, 2010: http://dictionary.reference.com/browse/moiety.*
Mickle J.E., Genotype-phenotype relationships in cystic fibrosis. Medical Clinicls of North America, 2000, vol. 84, No. 3, p. 597-607.*
Aranson B.G.W., Long-term expeirrence with inteferon beta-1b (Betaferon) in multiple sclerosis. J. Neurol., 2005, vol. 252 [Suppl 3]: III/28-III/33.*
Webster, et al, "Pegylation of Somatropin (Recombinant Human Growth Hormone): Impact on Its Clearance in Humans", Xenobiotica, Oct. 2008; 38(10): 1340-1351.
Definition of moiety from http://dictionary.reference.com/browse/moiety, pp. 1-3. Accessed Aug. 26, 2010.
Rudinger J, "Characteristics of the amino acids as components of a peptide hormone sequence," Peptide Hormones, JA Parsons Edition, University Park Press, Jun. 1976, pp. 1-7.
"Designing Custom Peptides," from SIGMA Genosys, pp. 1-2. Accessed Dec. 16, 2004.
Schinzel R, Drueckes P, "The phosphate recognition site of *Escherichia coli* maltodextrin phosphorylase," FEBS, Jul. 1991, 286(1,2): 125-128.
Berendsen HJC, "A Glimpse of the Holy Grail?" Science, 1998, 282: 642-643.
Voet D, Voet JG, Biochemistry, Second Edition, John Wiley & Sons, Inc., 1995, pp. 235-241.
Ngo JT, Marks J, Karplus M, "Computational Complexity, Protein Structure Prediction, and the Levinthal Paradox," The Protein Folding Problem and Tertiary Structure Prediction, K. Merc Jr. and S. Le Grand Edition, 1994, pp. 491-495.
Bradley CM, Barrick D, "Limits of Cooperativity in a Structurally Modular Protein: Response of the Notch Ankyrin Domain to Analogous Alanine Substitutions in Each Repeat," J. Mol. Biol., 2002, 324: 373-386.
Pascal Bailon et al., Rational Design of a Potent, Long-Lasting Form of Interferon: A 40kDa Branched Polyethylene Glycol-Conjugated Interferon alpha-2a for the Treatment of Hepatitis C,Bioconjugate Chemistry, Feb. 16, 2001, vol. 12, pp. 195-202.
Jing Li and W.John Kao, Synthesis of Polyethylene Glycol(PEG) Derivatives and PEGylated-Peptide Biopolymer Conjugate, Biomacromolecules, May 17, 2003. vol. 4, pp. 1055-1067.
Samuel Zalipsky, Chemistry of Polyethylene Glycol Conjugates with Biologically Active Molecules, Advanced Drug Delivery Reviews, Sep. 30, 1995, vol. 16, pp. 157-182.

* cited by examiner

*Primary Examiner* — Robert Landsman
*Assistant Examiner* — Bruce D Hissong
(74) *Attorney, Agent, or Firm* — Occhiuti Rohlicek & Tsao LLP

(57) ABSTRACT

This invention relates to a conjugate of a polymer moiety and an interferon-β moiety, an erythropoietin moiety, or a growth hormone moiety.

18 Claims, No Drawings

SEQUENCE LISTING

```
<160> NUMBER OF SEQ ID NOS: 8

<210> SEQ ID NO 1
<211> LENGTH: 187
<212> TYPE: PRT
<213> ORGANISM: Homo sapiens
<220> FEATURE:
<221> NAME/KEY: SIGNAL
<222> LOCATION: (1)..(21)

<400> SEQUENCE: 1

Met Thr Asn Lys Cys Leu Leu Gln Ile Ala Leu Leu Leu Cys Phe Ser
1               5                   10                  15

Thr Thr Ala Leu Ser Met Ser Tyr Asn Leu Leu Gly Phe Leu Gln Arg
            20                  25                  30

Ser Ser Asn Phe Gln Cys Gln Lys Leu Leu Trp Gln Leu Asn Gly Arg
        35                  40                  45

Leu Glu Tyr Cys Leu Lys Asp Arg Met Asn Phe Asp Ile Pro Glu Glu
    50                  55                  60

Ile Lys Gln Leu Gln Gln Phe Gln Lys Glu Asp Ala Ala Leu Thr Ile
65                  70                  75                  80

Tyr Glu Met Leu Gln Asn Ile Phe Ala Ile Phe Arg Gln Asp Ser Ser
                85                  90                  95

Ser Thr Gly Trp Asn Glu Thr Ile Val Glu Asn Leu Leu Ala Asn Val
            100                 105                 110

Tyr His Gln Ile Asn His Leu Lys Thr Val Leu Glu Glu Lys Leu Glu
        115                 120                 125

Lys Glu Asp Phe Thr Arg Gly Lys Leu Met Ser Ser Leu His Leu Lys
    130                 135                 140

Arg Tyr Tyr Gly Arg Ile Leu His Tyr Leu Lys Ala Lys Glu Tyr Ser
145                 150                 155                 160
```

```
His Cys Ala Trp Thr Ile Val Arg Val Glu Ile Leu Arg Asn Phe Tyr
            165                 170                 175

Phe Ile Asn Arg Leu Thr Gly Tyr Leu Arg Asn
            180                 185
```

<210> SEQ ID NO 2
<211> LENGTH: 212
<212> TYPE: PRT
<213> ORGANISM: Homo sapiens

<400> SEQUENCE: 2

```
Met Asn Ser Phe Ser Thr Ser Ala Phe Gly Pro Val Ala Phe Ser Leu
1               5                   10                  15

Gly Leu Leu Leu Val Leu Pro Ala Ala Phe Pro Ala Pro Val Pro Pro
                20                  25                  30

Gly Glu Asp Ser Lys Asp Val Ala Ala Pro His Arg Gln Pro Leu Thr
            35                  40                  45

Ser Ser Glu Arg Ile Asp Lys Gln Ile Arg Tyr Ile Leu Asp Gly Ile
    50                  55                  60

Ser Ala Leu Arg Lys Glu Thr Cys Asn Lys Ser Asn Met Cys Glu Ser
65                  70                  75                  80

Ser Lys Glu Ala Leu Ala Glu Asn Asn Leu Asn Leu Pro Lys Met Ala
                85                  90                  95

Glu Lys Asp Gly Cys Phe Gln Ser Gly Phe Asn Glu Glu Thr Cys Leu
            100                 105                 110

Val Lys Ile Ile Thr Gly Leu Leu Glu Phe Glu Val Tyr Leu Glu Tyr
        115                 120                 125

Leu Gln Asn Arg Phe Glu Ser Ser Glu Glu Gln Ala Arg Ala Val Gln
130                 135                 140

Met Ser Thr Lys Val Leu Ile Gln Phe Leu Gln Lys Lys Ala Lys Asn
145                 150                 155                 160

Leu Asp Ala Ile Thr Thr Pro Asp Pro Thr Thr Asn Ala Ser Leu Leu
                165                 170                 175

Thr Lys Leu Gln Ala Gln Asn Gln Trp Leu Gln Asp Met Thr Thr His
            180                 185                 190

Leu Ile Leu Arg Ser Phe Lys Glu Phe Leu Gln Ser Ser Leu Arg Ala
        195                 200                 205

Leu Arg Gln Met
            210
```

<210> SEQ ID NO 3
<211> LENGTH: 165
<212> TYPE: PRT
<213> ORGANISM: Artificial Sequence
<220> FEATURE:
<223> OTHER INFORMATION: Recombinant INF-beta with serine in place of
      cysteine at position 17 in the native mature INF-beta sequence

<400> SEQUENCE: 3

```
Ser Tyr Asn Leu Leu Gly Phe Leu Gln Arg Ser Ser Asn Phe Gln Ser
1               5                   10                  15

Gln Lys Leu Leu Trp Gln Leu Asn Gly Arg Leu Glu Tyr Cys Leu Lys
                20                  25                  30

Asp Arg Met Asn Phe Asp Ile Pro Glu Glu Ile Lys Gln Leu Gln Gln
            35                  40                  45

Phe Gln Lys Glu Asp Ala Ala Leu Thr Ile Tyr Glu Met Leu Gln Asn
    50                  55                  60

Ile Phe Ala Ile Phe Arg Gln Asp Ser Ser Ser Thr Gly Trp Asn Glu
```

```
                65                  70                  75                  80
Thr Ile Val Glu Asn Leu Leu Ala Asn Val Tyr His Gln Ile Asn His
                    85                  90                  95
Leu Lys Thr Val Leu Glu Glu Lys Leu Glu Lys Glu Asp Phe Thr Arg
                    100                 105                 110
Gly Lys Leu Met Ser Ser Leu His Leu Lys Arg Tyr Tyr Gly Arg Ile
                    115                 120                 125
Leu His Tyr Leu Lys Ala Lys Glu Tyr Ser His Cys Ala Trp Thr Ile
                    130                 135                 140
Val Arg Val Glu Ile Leu Arg Asn Phe Tyr Phe Ile Asn Arg Leu Thr
145                 150                 155                 160
Gly Tyr Leu Arg Asn
                165

<210> SEQ ID NO 4
<211> LENGTH: 193
<212> TYPE: PRT
<213> ORGANISM: Homo sapiens

<400> SEQUENCE: 4

Met Gly Val His Glu Cys Pro Ala Trp Leu Trp Leu Leu Leu Ser Leu
1               5                   10                  15
Leu Ser Leu Pro Leu Gly Leu Pro Val Leu Gly Ala Pro Pro Arg Leu
                20                  25                  30
Ile Cys Asp Ser Arg Val Leu Glu Arg Tyr Leu Leu Glu Ala Lys Glu
                35                  40                  45
Ala Glu Asn Ile Thr Thr Gly Cys Ala Glu His Cys Ser Leu Asn Glu
50                  55                  60
Asn Ile Thr Val Pro Asp Thr Lys Val Asn Phe Tyr Ala Trp Lys Arg
65                  70                  75                  80
Met Glu Val Gly Gln Gln Ala Val Glu Val Trp Gln Gly Leu Ala Leu
                    85                  90                  95
Leu Ser Glu Ala Val Leu Arg Gly Gln Ala Leu Leu Val Asn Ser Ser
                    100                 105                 110
Gln Pro Trp Glu Pro Leu Gln Leu His Val Asp Lys Ala Val Ser Gly
                    115                 120                 125
Leu Arg Ser Leu Thr Thr Leu Leu Arg Ala Leu Gly Ala Gln Lys Glu
                    130                 135                 140
Ala Ile Ser Pro Pro Asp Ala Ala Ser Ala Ala Pro Leu Arg Thr Ile
145                 150                 155                 160
Thr Ala Asp Thr Phe Arg Lys Leu Phe Arg Val Tyr Ser Asn Phe Leu
                    165                 170                 175
Arg Gly Lys Leu Lys Leu Tyr Thr Gly Glu Ala Cys Arg Thr Gly Asp
                    180                 185                 190
Arg

<210> SEQ ID NO 5
<211> LENGTH: 166
<212> TYPE: PRT
<213> ORGANISM: Homo sapiens

<400> SEQUENCE: 5

Ala Pro Pro Arg Leu Ile Cys Asp Ser Arg Val Leu Glu Arg Tyr Leu
1               5                   10                  15
Leu Glu Ala Lys Glu Ala Glu Asn Ile Thr Thr Gly Cys Ala Glu His
                20                  25                  30
```

Cys Ser Leu Asn Glu Asn Ile Thr Val Pro Asp Thr Lys Val Asn Phe
            35                  40                  45

Tyr Ala Trp Lys Arg Met Glu Val Gly Gln Gln Ala Val Glu Val Trp
 50                  55                  60

Gln Gly Leu Ala Leu Leu Ser Glu Ala Val Leu Arg Gly Gln Ala Leu
 65                  70                  75                  80

Leu Val Asn Ser Ser Gln Pro Trp Glu Pro Leu Gln Leu His Val Asp
                 85                  90                  95

Lys Ala Val Ser Gly Leu Arg Ser Leu Thr Thr Leu Leu Arg Ala Leu
                100                 105                 110

Gly Ala Gln Lys Glu Ala Ile Ser Pro Pro Asp Ala Ala Ser Ala Ala
                115                 120                 125

Pro Leu Arg Thr Ile Thr Ala Asp Thr Phe Arg Lys Leu Phe Arg Val
            130                 135                 140

Tyr Ser Asn Phe Leu Arg Gly Lys Leu Lys Leu Tyr Thr Gly Glu Ala
145                 150                 155                 160

Cys Arg Thr Gly Asp Arg
                165

<210> SEQ ID NO 6
<211> LENGTH: 217
<212> TYPE: PRT
<213> ORGANISM: Homo sapiens

<400> SEQUENCE: 6

Met Ala Thr Gly Ser Arg Thr Ser Leu Leu Leu Ala Phe Gly Leu Leu
 1               5                  10                  15

Cys Leu Pro Trp Leu Gln Glu Gly Ser Ala Phe Pro Thr Ile Pro Leu
                20                  25                  30

Ser Arg Leu Phe Asp Asn Ala Met Leu Arg Ala His Arg Leu His Gln
            35                  40                  45

Leu Ala Phe Asp Thr Tyr Gln Glu Phe Glu Ala Tyr Ile Pro Lys Glu
 50                  55                  60

Gln Lys Tyr Ser Phe Leu Gln Asn Pro Gln Thr Ser Leu Cys Phe Ser
65                  70                  75                  80

Glu Ser Ile Pro Thr Pro Ser Asn Arg Glu Glu Thr Gln Gln Lys Ser
                85                  90                  95

Asn Leu Glu Leu Leu Arg Ile Ser Leu Leu Leu Ile Gln Ser Trp Leu
            100                 105                 110

Glu Pro Val Gln Phe Leu Arg Ser Val Phe Ala Asn Ser Leu Val Tyr
        115                 120                 125

Gly Ala Ser Asp Ser Asn Val Tyr Asp Leu Leu Lys Asp Leu Glu Glu
130                 135                 140

Gly Ile Gln Thr Leu Met Gly Arg Leu Glu Asp Gly Ser Pro Arg Thr
145                 150                 155                 160

Gly Gln Ile Phe Lys Gln Thr Tyr Ser Lys Phe Asp Thr Asn Ser His
                165                 170                 175

Asn Asp Asp Ala Leu Leu Lys Asn Tyr Gly Leu Leu Tyr Cys Phe Arg
            180                 185                 190

Lys Asp Met Asp Lys Val Glu Thr Phe Leu Arg Ile Val Gln Cys Arg
        195                 200                 205

Ser Val Glu Gly Ser Cys Gly Phe
    210                 215

<210> SEQ ID NO 7
<211> LENGTH: 191

```
<212> TYPE: PRT
<213> ORGANISM: Homo sapiens

<400> SEQUENCE: 7

Phe Pro Thr Ile Pro Leu Ser Arg Leu Phe Asp Asn Ala Met Leu Arg
1               5                   10                  15

Ala His Arg Leu His Gln Leu Ala Phe Asp Thr Tyr Gln Glu Phe Glu
                20                  25                  30

Glu Ala Tyr Ile Pro Lys Glu Gln Lys Tyr Ser Phe Leu Gln Asn Pro
            35                  40                  45

Gln Thr Ser Leu Cys Phe Ser Glu Ser Ile Pro Thr Pro Ser Asn Arg
        50                  55                  60

Glu Glu Thr Gln Gln Lys Ser Asn Leu Glu Leu Leu Arg Ile Ser Leu
65                  70                  75                  80

Leu Leu Ile Gln Ser Trp Leu Glu Pro Val Gln Phe Leu Arg Ser Val
                85                  90                  95

Phe Ala Asn Ser Leu Val Tyr Gly Ala Ser Asp Ser Asn Val Tyr Asp
            100                 105                 110

Leu Leu Lys Asp Leu Glu Glu Gly Ile Gln Thr Leu Met Gly Arg Leu
        115                 120                 125

Glu Asp Gly Ser Pro Arg Thr Gly Gln Ile Phe Lys Gln Thr Tyr Ser
130                 135                 140

Lys Phe Asp Thr Asn Ser His Asn Asp Asp Ala Leu Leu Lys Asn Tyr
145                 150                 155                 160

Gly Leu Leu Tyr Cys Phe Arg Lys Asp Met Asp Lys Val Glu Thr Phe
                165                 170                 175

Leu Arg Ile Val Gln Cys Arg Ser Val Glu Gly Ser Cys Gly Phe
            180                 185                 190

<210> SEQ ID NO 8
<211> LENGTH: 192
<212> TYPE: PRT
<213> ORGANISM: Artificial Sequence
<220> FEATURE:
<223> OTHER INFORMATION: Modified human INF-beta with an additional
      methionine attached to the N-terminus of the native mature
      INF-beta.

<400> SEQUENCE: 8

Met Phe Pro Thr Ile Pro Leu Ser Arg Leu Phe Asp Asn Ala Met Leu
1               5                   10                  15

Arg Ala His Arg Leu His Gln Leu Ala Phe Asp Thr Tyr Gln Glu Phe
                20                  25                  30

Glu Glu Ala Tyr Ile Pro Lys Glu Gln Lys Tyr Ser Phe Leu Gln Asn
            35                  40                  45

Pro Gln Thr Ser Leu Cys Phe Ser Glu Ser Ile Pro Thr Pro Ser Asn
        50                  55                  60

Arg Glu Glu Thr Gln Gln Lys Ser Asn Leu Glu Leu Leu Arg Ile Ser
65                  70                  75                  80

Leu Leu Leu Ile Gln Ser Trp Leu Glu Pro Val Gln Phe Leu Arg Ser
                85                  90                  95

Val Phe Ala Asn Ser Leu Val Tyr Gly Ala Ser Asp Ser Asn Val Tyr
            100                 105                 110

Asp Leu Leu Lys Asp Leu Glu Glu Gly Ile Gln Thr Leu Met Gly Arg
        115                 120                 125

Leu Glu Asp Gly Ser Pro Arg Thr Gly Gln Ile Phe Lys Gln Thr Tyr
130                 135                 140
```

```
Ser Lys Phe Asp Thr Asn Ser His Asn Asp Asp Ala Leu Leu Lys Asn
145                 150                 155                 160

Tyr Gly Leu Leu Tyr Cys Phe Arg Lys Asp Met Asp Lys Val Glu Thr
                165                 170                 175

Phe Leu Arg Ile Val Gln Cys Arg Ser Val Glu Gly Ser Cys Gly Phe
            180                 185                 190
```

PROTEIN-POLYMER CONJUGATES

CROSS-REFERENCE TO RELATED APPLICATION PARAGRAPH

This application claims the benefit of U.S. Provisional Application No. 61/085,072 filed on Jul. 31, 2008, the content of which is hereby incorporated by reference in its entirety.

BACKGROUND

Advance in cell biology and recombinant protein technologies has led to the development of protein therapeutics. Yet, major hurdles still exist. Most proteins are susceptible to proteolytic degradation and therefore have a short circulating time. Other disadvantages include low water solubility and inducement of neutralizing antibodies.

Attachment of a polymer, e.g., polyethylene glycol (PEG), to a protein hinders access of proteolytic enzymes to the protein backbone, resulting in enhanced protein stability. In addition, it may also improve water solubility and minimize immuogenicity. There is a need for effective methods of attaching polymer to proteins.

SUMMARY

An aspect of the present invention relates to polymer-polypeptide conjugates of formula I:

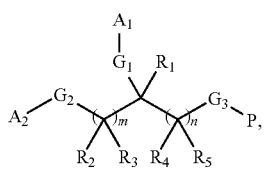

formula I wherein each of $R_1$, $R_2$, $R_3$, $R_4$, and $R_5$, independently, is H, $C_{1-10}$ alkyl, $C_{2-10}$ alkenyl, $C_{2-10}$ alkynyl, aryl, heteraryl, $C_{3-8}$ cycloalkyl, or $C_{3-8}$ heterocycloalkyl; each of $A_1$ and $A_2$, independently, is a polymer moiety (e.g., a polyalkylene oxide moiety); each of $G_1$, $G_2$, and $G_3$, independently, is a bond or a linking functional group; P is an interferon-β (INF-β) moiety, an erythropoietin (EPO) moiety, or a growth hormone (GH) moiety; m is 0 or an integer of 1-10; and n is an integer of 1-10. In these conjugates, the N-terminus of the INF-β moiety, the EPO moiety, or the GH moiety is bonded to $G_3$.

Referring to the above formula, the polymer-polypeptide conjugates have one or more of the following features: $A_1$ and $A_2$ are polyalkylene oxide moieties having a molecular weight of 2-100 kD (preferably 10-30 kD, e.g., 20 kD); each of $G_1$ and $G_2$ is

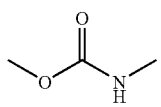

(in which the O atom is bonded to $A_1$ or $A_2$, and the N atom is bonded to a carbon atom as shown in formula I; each of $G_1$ and $G_2$ is urea, sulfonamide, or amide (in which the N atom is bonded to a carbon atom as shown in formula I); m is 4; n is 2; and each of $R_1$, $R_2$, $R_3$, $R_4$, and $R_5$ is H. In some of these conjugates, P is rINF-β $Ser_{17}$ or a modified INF-β moiety containing 1-4 additional amino acid residues at the N-terminus of the INF-β.

Another aspect of the present invention relates to polymer-peptide conjugates of formula II:

$$A\text{-}G_1\text{-}L\text{-}G_2\text{-}P, \qquad \text{formula II}$$

wherein A is a polymer moiety (e.g., a polyalkylene oxide moiety); each of $G_1$ and $G_2$, independently, is a bond or a linking functional group; L is $C_{2-10}$ alkenylene or $C_{2-10}$ alkynylene; and P is an INF-β moiety, an EPO moiety, or a GH moiety. In these conjugates, the N-terminus of the INF-β moiety, the EPO moiety, or the GH moiety is attached to $G_2$.

Referring to formula II, the polymer-peptide conjugates have one or more of the following features: $A_1$ and $A_2$ are polyalkylene oxide moieties having a molecular weight of 2-100 kD (preferably 10-30 kD, e.g., 20 kD), each of $G_1$ and $G_2$ is a bond, $C_6$ is alkenylene, and each of $R_1$, $R_2$, $R_3$, $R_4$, and $R_5$ is H.

Another aspect of the present invention relates to polymer-peptide conjugates of formula III:

formula III wherein each of $R_1$, $R_2$, $R_3$, and $R_4$, independently, is H, $C_{1-10}$ alkyl, $C_{2-10}$ alkenyl, $C_{2-10}$ alkynyl, aryl, heteraryl, $C_{3-8}$ cycloalkyl, or $C_{3-8}$ heterocycloalkyl; n is an integer of 2-10; A is a polymer moiety; G is a linking functional group; and P is a peptide moiety, the nitrogen atom of the N-terminus of the peptide moiety being bonded to the carbon atom in the

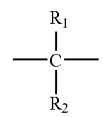

moiety shown in the formula above.

Referring to formula II, the polymer-peptide conjugates have one or more of the following features: n is 1; A is polyalkylene oxide moieties having a molecular weight of 10-40 kD or 20-30 kD; G is

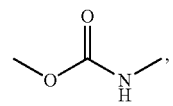

in which the O atom is bonded to A, and the N atom is bonded to a carbon atom; and P is an INF moiety, an EPO moiety, a GH moiety.

The term "$C_{1-10}$ alkyl" used herein refers to a straight-chained or branched hydrocarbon mono-valent radical containing 1 to 10 carbon atoms. Examples of alkyl groups include methyl, ethyl, n-propyl, isopropyl, tert-butyl, and n-pentyl. Similarly, the term "$C_{2-10}$ alkenyl" refers to a straight-chained or branched hydrocarbon mono-valent radical containing 2 to 10 carbon atoms and one or more double bonds. The term "$C_{2-10}$ alkynyl" refers to a straight-chained or branched hydrocarbon mono-valent radical containing 2 to 10 carbon atoms and one or more triple bonds. The term "$C_{2-10}$ alkenylene" refers to a straight-chained or branched hydrocarbon bi-valent radical containing 2 to 10 carbon atoms and one or more double bonds. The term "$C_{2-10}$ alkynylene" refers to a straight-chained or branched hydrocarbon bi-valent radical containing 2 to 10 carbon atoms and one or more triple bonds.

The term "aryl" used herein refers to a hydrocarbon ring system (mono-cyclic or bi-cyclic) having at least one aromatic ring. Examples of aryl moieties include, but are not limited to, phenyl, naphthyl, and pyrenyl.

The term "heteroaryl" used herein refers to a hydrocarbon ring system (mono-cyclic or bi-cyclic) having at least one aromatic ring which contains at least one heteroatom such as O, N, or S as part of the ring system and the reminder being carbon. Examples of heteroaryl moieties include, but are not limited to, furyl, pyrrolyl, thienyl, oxazolyl, imidazolyl, thiazolyl, pyridinyl, pyrimidinyl, quinazolinyl, and indolyl.

The term "cycloalkyl" used herein refers to a partially or fully saturated mono-cyclic or bi-cyclic ring system having only carbon ring atoms. Examples include, but are not limited to, cyclopropanyl, cyclopentanyl, and cyclohexanyl.

The term "heterocycloalkyl" used herein refers to a partially or fully saturated mono-cyclic or bi-cyclic ring system having, in addition to carbon, one or more heteroatoms (e.g., O, N, or S), as ring atoms. Examples include, but are not limited to, piperidine, piperazine, morpholine, thiomorpholine, and 1,4-oxazepane.

Alkyl, alkenyl, alkynyl, alkenylene, alkynylene, aryl, heteroaryl, cycloalkyl, and heterocycloalkyl mentioned herein include both substituted and unsubstituted moieties. Examples of substituents include $C_1$-$C_{10}$ alkyl, $C_2$-$C_{10}$ alkenyl, $C_2$-$C_{10}$ alkynyl, $C_3$-$C_8$ cycloalkyl, $C_5$-$C_8$ cycloalkenyl, $C_1$-$C_{10}$ alkoxy, aryl, aryloxy, heteroaryl, heteroaryloxy, amino, $C_1$-$C_{10}$ alkylamino, $C_1$-$C_{20}$ dialkylamino, arylamino, diarylamino, hydroxyamino, alkoxyamino, $C_1$-$C_{10}$ alkylsulfonamide, arylsulfonamide, hydroxy, halogen, thio, $C_1$-$C_{10}$ alkylthio, arylthio, cyano, nitro, acyl, acyloxy, carboxyl, and carboxylic ester.

The term "polymer moiety" refers to a mono-valent radical derived from linear, branched, or star-shaped polymer. The molecular weight of the polymer moiety may be 2-100 kD. Examples of the polymer moiety include, but are not limited to, polyethylene oxide, polyethylene glycol, polyisopropylene oxide, polybutenylene oxide, polyethylene glycol, and copolymers thereof Other polymers such as dextran, polyvinyl alcohols, polyacrylamides, or carbohydrate-based polymers can also be used as long as they are not antigenic, toxic, or eliciting immune response.

The term "polypeptide moiety" refers to a mono-valent radical derived from either a naturally occurring polypeptide or a modified polypeptide. The naturally occurring peptide can be INF-$\alpha_{2b}$, INF-$\beta$, GH, EPO, and granulocyte colon-stimulating factor, or antibody. The modified peptide can be, e.g., a peptide containing INF and 1-4 additional amino acid residues at the N-terminus of the INF-$\alpha_{2b}$. An example of such a modified INF is

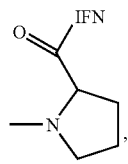

IFN representing an INF-$\alpha_{2b}$ moiety, the amino group at the N-terminus of which is bonded to the carbonyl group.

The term "interferon-$\beta$" refers to a family of highly homologous proteins that inhibit viral replication and cellular proliferation and modulate immune response. See Derynck et al., (1980). *Nature* 285 (5766): 542-7; and Taniguchi et al., (1980). *Gene* 10 (1): 11-5. It includes both naturally occurring INF-$\beta$s and their functional equivalents, i.e., a polypeptide having at least 80% (e.g., 85%, 90%, 95%, or 99%) identical to its wild-type counterpart. Examples of INF-$\beta$ include the active ingredients in the commercially available drugs, such as Avonex, Betaseron, and Rebif. See, e.g., Etemadifar M. et al., *Acta Neurol. Scand.*, 2006, 113(5): 283-7.

Listed below are amino acid sequences of exemplary human INF-$\beta$ proteins, either in precursor form or in mature form:

```
mtnkcllqia  lllcfsttal  smsynllgfl  qrssnfqcqk llwqlngrle  yclkdrmnfd  ipeeikqlqq  fqkedaalti yemlqnifai  frqdssstgw  netivenlla  nvyhqinhlk tvleekleke  dftrgklmss  lhlkryygri  lhylkakeys hcawtivrve  ilrnfyfinr  ltgylrn
```

(See GenBank Accession No.: M28622, the Apr. 27, 1993 version; italicized portion refers to the signal peptide)

```
mnsfstsafg  pvafslglll  vlpaafpapv  ppgedskdva aphrqpltss  eridkqiryi  ldgisalrke  tcnksnmces skealaennl  nlpkmaekdg  cfqsgfneet  clvkiitgll efevyleylq  nrfesseeqa  ravqmstkvl  iqflqkkakn ldaittpdpt  tnaslltklq  aqnqwlqdmt  thlilrsfke flqsslralr  qm
```

(See GenBank Accession No.: CAA00839, the Dec. 3, 1993 version)

In one example, the INF-$\beta$ is mutant rINF-$\beta$ Ser$_{17}$ (recombinant INF-$\beta$, in which serine is in place of cysteine at position 17 in the native mature INF-$\beta$ sequence). The amino acid of this mutant is shown below:

```
synllgflqr  ssnfqsqkll  wqlngrleyc  lkdrmnfdip eeikqlqqfq  kedaaltiye  mlqnifaifr  qdssstgwne tivenllanv  yhqinhlktv  leeklekedf  trgklmsslh lkryygrilh  ylkakeyshc  awtivrveil  rnfyfinrlt  gylrn
```

In another example, the INF-$\beta$ is a modified native INF-$\beta$, in which 1-4 additional amino acid residues are attached to the N-terminus of the native INF-$\beta$.

EPO, produced by either liver or kidney, is a glycoprotein hormone that controls erythropoiesis or red blood cell production. It includes both naturally occurring EPO and its functional equivalents. See U.S. Pat. No. 5,621,080 and US Patent Application Publication 20050176627. The amino acid sequences of human EPO (in precursor and mature form) are shown below:

```
mgvhecpawl wlllsllslp lglpvlgapp rlicdsrvle
rylleakeae nittgcaehc slnenitvpd tkvnfyawkr
mevgqqavev wqglallsea vlrgqallvn ssqpweplql
hvdkavsglr slttllralg aqkeaisppd aasaaplrti
tadtfrklfr vysnflrgkl klytgeacrt gdr (precursor)

apprlicdsr vlerylleak eaenittgca ehcslnenit
vpdtkvnfya wkrmevgqqa vevwqglall seavlrgqal
lvnssqpwep lqlhvdkavs glrslttllr algaqkeais
ppdaasaapl rtitadtfrk lfrvysnflr gklklytgea
crtgdr (mature form)
```

An EPO protein used to make the conjugate of this invention can be an EPO protein, either in precursor or mature form, produced by a suitable species, e.g., human, murine, swine, or bovine. In one example, the EPO protein has an amino acid sequence at least 80% (e.g., 85%, 90%, 95% or 99%) identical to one of the amino acid sequences shown above. In another example, the EPO is a modified native EPO in which 1-4 additional amino acid residues are attached to the N-terminus of the native EPO.

The term "growth hormone" refers to the naturally occurring human growth hormone, either in precursor or mature form, and its functional variants, i.e., having an amino acid sequence at least 80% (e.g., 85%, 90%, 95%, or 99%) identical to the naturally occurring human growth hormone and possessing the same physiological activity of that human growth hormone. In one example, the growth hormone is a modified native growth hormone in which 1-4 additional amino acid residues are attached to the N-terminus of the native growth hormone. The amino acid sequences of the naturally occurring human growth hormone (in precursor and mature form) are shown below:

```
matgsrtsll lafgllclpw lqegsafpti plsrlfdnam
lrahrlhqla fdtyqefeea yipkeqkysf lqnpqtslcf
sesiptpsnr eetqqksnle llrislllig swlepvqflr
svfanslvyg asdsnvydll kdleegiqtl mgrledgspr
tgqifkqtys kfdtnshndd allknyglly cfrkdmdkve
tflrivqcrs vegscgf (precursor)

fptiplsrlf dnamlrahrl hqlafdtyqe feeayipkeq
kysflqnpqt slcfsesipt psnreetqqk snlellrisl
lliqswlepv qflrsvfans lvygasdsnv ydllkdleeg
iqtlmgrled gsprtgqifk qtyskfdtns hnddallkny
gllycfrkdm dkvetflriv qcrsvegscg f (mature form)

mfptiplsrl fdnamlrahr lhqlafdtyq efeeayipke
qkysflqnpq tslcfsesip tpsnreetqq ksnlellris
llliqswlep vqflrsvfan slvygasdsn vydllkdlee
giqtlmgrle dgsprtgqif kqtyskfdtn shnddallkn
ygllycfrkd mdkvetflri vqcrsvegsc gf (modified form)
```

The "percent identity" of two amino acid sequences is determined using the algorithm of Karlin and Altschul *Proc. Natl. Acad. Sci. USA* 87:2264-68, 1990, modified as in Karlin and Altschul *Proc. Natl. Acad. Sci. USA* 90:5873-77, 1993. Such an algorithm is incorporated into the NBLAST and XBLAST programs (version 2.0) of Altschul, et al. *J. Mol. Biol.* 215:403-10, 1990. BLAST protein searches can be performed with the XBLAST program, score=50, wordlength=3 to obtain amino acid sequences homologous to the protein molecules for use in the invention. Where gaps exist between two sequences, Gapped BLAST can be utilized as described in Altschul et al, *Nucleic Acids Res.* 25(17):3389-3402, 1997. When utilizing BLAST and Gapped BLAST programs, the default parameters of the respective programs (e.g., XBLAST and NBLAST) can be used.

The term "linking functional group" refers to a bi-valent functional group, one end being connected to the polymer moiety and the other end being connected to the peptide moiety. Examples include, but are not limited to, —O—, —S—, carboxylic ester, carbonyl, carbonate, amide, carbamate, urea, sulfonyl, sulfinyl, amino, imino, hydroxyamino, phosphonate, or phosphate group.

The peptide-polymer conjugate described above can be in the free form or in the form of salt, if applicable. A salt, for example, can be formed between an anion and a positively charged group (e.g., amino) on a peptide-polymer conjugate of this invention. Suitable anions include chloride, bromide, iodide, sulfate, nitrate, phosphate, citrate, methanesulfonate, trifluoroacetate, and acetate. Likewise, a salt can also be formed between a cation and a negatively charged group (e.g., carboxylate) on a polypeptide-polymer conjugate of this invention. Suitable cations include sodium ion, potassium ion, magnesium ion, calcium ion, and an ammonium cation such as tetramethylammonium ion.

In addition, the peptide-polymer conjugate may have one or more double bonds, or one or more asymmetric centers. Such a conjugate can occur as racemates, racemic mixtures, single enantiomers, individual diastereomers, diastereomeric mixtures, and cis- or trans- or E- or Z-double bond isomeric forms.

Examples the polymer-peptide conjugate of this invention is shown below:

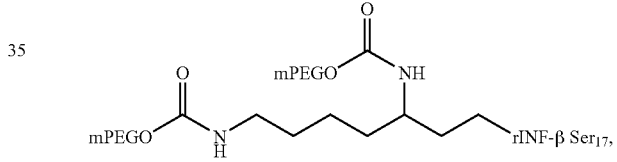

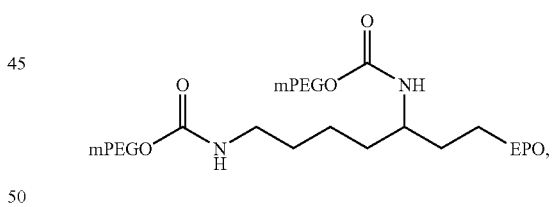

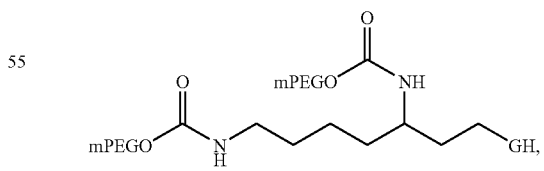

in which mPEG represents methoxy-capped polyethylene glycol having a molecular weight of 20 kD, and the N-termini of rINF-β $Ser_{17}$, EPO, and GH are attached to the rightmost carbon shown in the above structures.

Certain proteins have therapeutic utilities. The conjugates of this invention, containing a peptide moiety, can therefore be used to treat disease. For example, INF-β is an immunomodulating medication for treating HCV or HBV infection. See, e.g., *Journal of Vascular and Interventional Radiology* 13 (2002): 191-196. Thus, within the scope of this invention is a method of treating hepatitis C virus (HCV) infection or hepatitis B virus (HBV) infection with an INF-β-polymer conjugate described above. As another example, EPO is a hormone produced by the kidney to promote the formation of red blood cells in the bone marrow. It has been used as an immunomodulating medication for treating anaemia resulting from chronic kidney disease, anemia secondary to zidovudine treatment of AIDS, and anemia associated with cancer. Recent studies have also found that EPO enhances neurogenesis and plays a critical role in post-stroke recovery. See, e.g., P. T. Tsai, Journal of Neuroscience, 2006, 26: 1269. Thus, another aspect of this invention relates to a method of treating aneamia or enhancing neurogenesis by an EPO-polymer conjugate described above.

Also within the scope of this invention is a composition containing the INF-β-polymer conjugate described above for use in treating HCV infection or HBV infection, and a composition containing the EPO-polymer conjugate described above for use in treating aneamia or enhancing neurogenesis, as well as the therapeutic use and use of the conjugate for the manufacture of a medicament for treating HCV infection, HBV infection, or aneamia, or for enhancing neurogenesis.

The details of one or more embodiments of the invention are set forth in the description below. Other features, objects, and advantages of the invention will be apparent from the description and from the claims.

DETAILED DESCRIPTION

The peptide-polymer conjugates of the present invention can be prepared by synthetic methods well known in the chemical art. For example, one can combine a linker molecule having one or more active functional groups with two polymer molecules having a functional group reactive to those on the linker molecule. Subsequently, a peptide molecule containing a functional group is reacted with a functional group of the linker molecule to form a peptide-polymer conjugate of this invention. Two illustrative synthetic schemes are provided herein.

Scheme 1 below shows an example of preparing the peptide-polymer conjugates of formula I. Diamine compound 1, which contains an acetal group, is reacted with N-hydroxysuccinimidyl carbonate mPEG (i.e., compound 2) to form di-PEGylated compound 3, which is subsequently converted to aldehyde 4. This aldehyde compound is reacted with peptide H—P having a free amino group via reductive alkylation to afford a peptide-polymer conjugate of this invention.

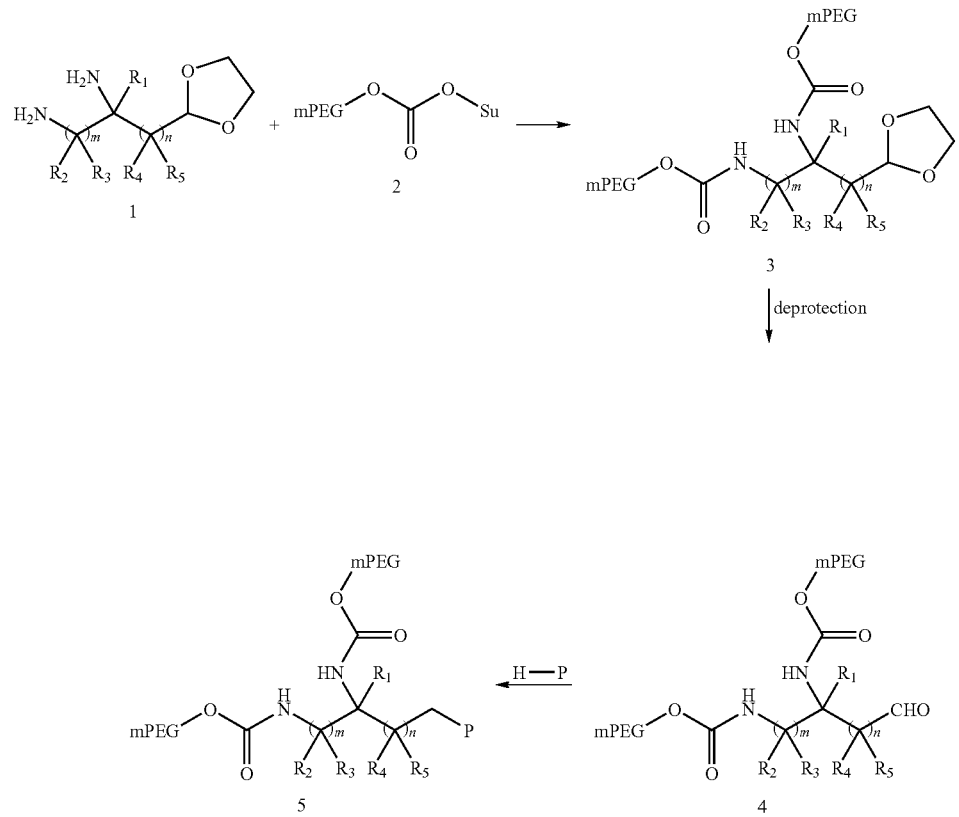

Scheme 2 below shows an example of preparing the peptide-polymer conjugates of formula II. Chemical 6 has a polymer moiety and an aldehyde functional group. It can be reacted with peptide 7, which has a free amino functional group. The resulting product 8 is subsequently reduced, e.g., by hydrogenation or by NaBH$_3$CN, to afford peptide-polymer conjugate 9.

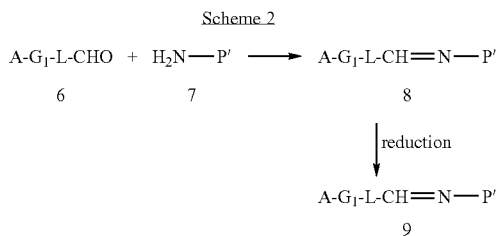

A is a polymer moiety
G$_1$ is a bond or a linking functional group
L is alkenylene or alkynylene
H$_2$N—P' is INF-β, EPO, or GH Scheme 3 below is an example of preparing a peptide-polymer conjugate of formula III. Compound 10 having an acetal group, which can be prepared from β-amino acid, is reacted with N-hydroxysuccinimidyl carbonate mPEG 2 to form PEGylated compound 11, which is subsequently converted to aldehyde 12. This aldehyde compound is reacted with peptide H—P having a free amino group via reductive alkylation to afford desired compound 13.

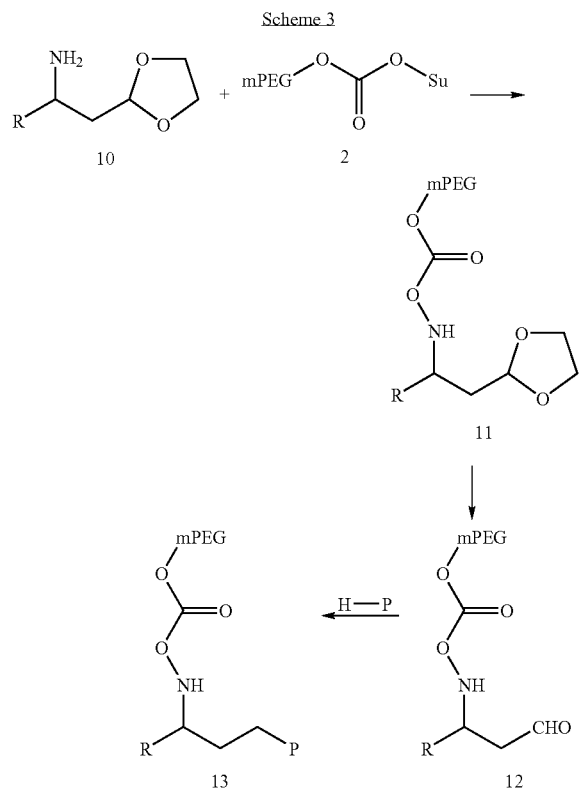

The chemical reactions described above include using solvents, reagents, catalysts, protecting group and deprotecting group reagents, and certain reaction conditions. They may additionally include steps, either before or after the steps described specifically herein, to add or remove suitable protecting groups in order to ultimately allow for synthesis of a peptide-polymer conjugate. In addition, various synthetic steps may be performed in an alternate sequence or order to give the desired polypeptide-polymer conjugates. Synthetic chemistry transformations and protecting group methodologies (protection and deprotection) useful in synthesizing applicable peptide-polymer conjugates are known in the art and include, for example, those described in R. Larock, *Comprehensive Organic Transformations*, VCH Publishers (1989); T. W. Greene and P. G. M. Wuts, *Protective Groups in Organic Synthesis*, 2d. Ed., John Wiley and Sons (1991); L. Fieser and M. Fieser, *Fieser and Fieser's Reagents for Organic Synthesis*, John Wiley and Sons (1994); and L. Paquette, ed., *Encyclopedia of Reagents for Organic Synthesis*, John Wiley and Sons (1995) and subsequent editions thereof.

A peptide-polymer conjugate thus synthesized can be further purified by a method such as ion exchange chromatography, gel filtration chromatography, electrophoresis, dialysis, ultrafiltration, or ultracentrifugation.

The peptide-polymer conjugate of the invention may be pharmaceutically active in the conjugate form. Alternatively, it can release a pharmaceutically active peptide in vivo (e.g., through hydrolysis) by enzymatically cleaving the linkage between the peptide moiety and the polymer moiety. Examples of enzymes involved in in vivo cleaving linkages include oxidative enzymes (e.g., peroxidases, amine oxidases, or dehydrogenases), reductive enzymes (e.g., keto reductases), and hydrolytic enzymes (e.g., proteases, esterases, sulfatases, or phosphatases).

Thus, one aspect of this invention relates to a method of administering an effective amount of one or more of the above-described peptide-polymer conjugates for treating a disorder (e.g., HCV or HBV infection, or aneamia). Specifically, a disease can be treated by administering to a subject one or more of the peptide-polymer conjugates in an effective amount. Such a subject can be identified by a health care professional based on results from any suitable diagnostic method.

As used herein, the term "treating" or "treatment" is defined as the application or administration of a composition including a peptide-polymer conjugate to a subject (human or animal), who has a disorder, a symptom of the disorder, a disease or disorder secondary to the disorder, or a predisposition toward the disorder, with the purpose to cure, alleviate, relieve, remedy, or ameliorate the disorder, the symptom of the disorder, the disease or disorder secondary to the disorder, or the predisposition toward the disorder. "An effective amount" refers to an amount of a peptide-polymer conjugate which confers a therapeutic effect on the treated subject. The therapeutic effect may be objective (i.e., measurably by some tests or markers) or subjective (i.e., a subject gives an indication of or feels an effect).

To practice the method of the present invention, a composition having one or more of the above-mentioned conjugates can be administered parenterally, orally, nasally, rectally, topically, or buccally. The term "parenteral" as used herein refers to subcutaneous, intracutaneous, intravenous, intramuscular, intraarticular, intraarterial, intrasynovial, intrasternal, intrathecal, intralesional, intraperitoneal, intratracheal or intracranial injection, as well as any suitable infusion technique.

A sterile injectable composition can be a solution or suspension in a non-toxic parenterally acceptable diluent or solvent, such as a solution in 1,3-butanediol. Among the acceptable vehicles and solvents that can be employed are mannitol, water, Ringer's solution, and isotonic sodium chloride solution. In addition, fixed oils are conventionally employed as a solvent or suspending medium (e.g., synthetic mono- or di-glycerides). Fatty acid, such as oleic acid and its glyceride derivatives are useful in the preparation of injectables, as are natural pharmaceutically acceptable oils, such as olive oil or castor oil, especially in their polyoxyethylated versions. These oil solutions or suspensions can also contain a long chain alcohol diluent or dispersant, or carboxymethyl cellulose or similar dispersing agents. Other commonly used surfactants such as Tweens or Spans or other similar emulsifying agents or bioavailability enhancers which are commonly used in the manufacture of pharmaceutically acceptable solid, liquid, or other dosage forms can also be used for the purpose of formulation.

A composition for oral administration can be any orally acceptable dosage form including capsules, tablets, emulsions, and aqueous suspensions, dispersions, and solutions. In the case of tablets, commonly used carriers include lactose and corn starch. Lubricating agents, such as magnesium stearate, are also typically added. For oral administration in a capsule form, useful diluents include lactose and dried corn starch. When aqueous suspensions or emulsions are administered orally, the active ingredient can be suspended or dissolved in an oily phase combined with emulsifying or suspending agents. If desired, certain sweetening, flavoring, or coloring agents can be added.

A nasal aerosol or inhalation composition can be prepared according to techniques well known in the art of pharmaceutical formulation. For example, such a composition can be prepared as a solution in saline, employing benzyl alcohol or other suitable preservatives, absorption promoters to enhance bioavailability, fluorocarbons, and/or other solubilizing or dispersing agents known in the art. A composition having one or more of the above-described compounds can also be administered in the form of suppositories for rectal administration.

A pharmaceutically acceptable carrier is routinely used with one or more active above-mentioned conjugates. The carrier in the pharmaceutical composition must be "acceptable" in the sense that it is compatible with the active ingredient of the composition (and preferably, capable of stabilizing the active ingredient) and not deleterious to the subject to be treated. One or more solubilizing agents can be utilized as pharmaceutical excipients for delivery of an above-mentioned compound. Examples of other carriers include colloidal silicon oxide, magnesium stearate, cellulose, sodium lauryl sulfate, and D&C Yellow # 10.

The examples below are to be construed as merely illustrative, and not limitative of the remainder of the disclosure in any way whatsoever. Without further elaboration, it is believed that one skilled in the art can, based on the description herein, utilize the present invention to its fullest extent. All publications cited herein are hereby incorporated by reference in their entirety.

EXAMPLE 1

IFN-β-di-PEG polymer conjugate

Preparation of di-PEG aldehyde

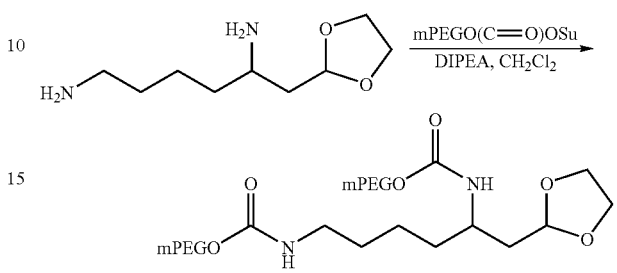

20 kD PEGO(C=O)OSu was prepared from 20 kD mPE-GOH purchased from (SunBio Inc., CA, USA) according to the method described in Bioconjugate Chem. 1993, 4, 568-569.

A solution of 6-(1,3-dioxolan-2-yl)hexane-1,5-diamine in dichloromethane (11.97 g of the solution containing 9.03 mg of diamine, 47.8 μmol) was added to a flask containing 20 kD PEGO(C=O)OSu (1.72 g, 86.0 μmol). After PEGO(C=O)OSu was completely dissolved, N,N-diisopropylethylamine (79 μL, 478 μmol) was added. The reaction mixture was stirred at room temperature for 24 h, and then methyl t-butyl ether (200 mL) was added dropwise with stirring. The resulting precipitate was collected and dried under vacuum to give di-PEG acetal (1.69 g, 98%) as a white solid.

$^1$H NMR (400 MHz, $d_6$-DMSO) δ 7.16 (t, J=5.2 Hz, 1H), 7.06 (d, J=8.8 Hz, 1H), 4.76 (t, J=4.8 Hz, 1H), 4.10-3.95 (m, 4H), 1.80-1.65 (m, 1H), 1.65-1.50 (m, 1H), 1.48-1.10 (m, 6H).

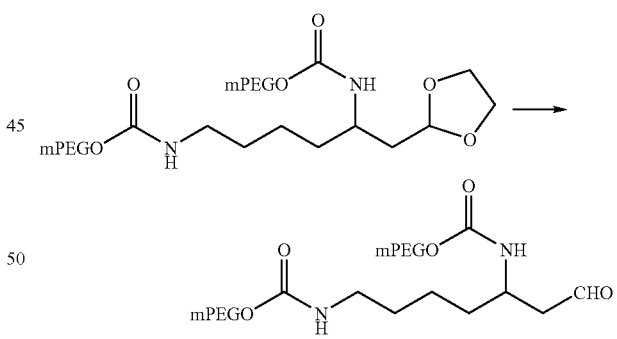

Di-PEG acetal (4.0 g, 0.2 mmol) was suspended in pH 2.0 buffer (critic acid, 40 mL). The reaction mixture was stirred at 35° C. for 24 h and then extracted with dichloromethane (3×50 mL). The combined organic layers were dried over magnesium sulfate, concentrated, and then re-dissolved in dichloromethane (20 mL). The solution was added dropwisely to methyl t-butyl ether (400 mL) with stirring. The resulting precipitate was collected and dried at reduced pressure to give di-PEG aldehyde (3.8 g, 95%) as a white solid.

$^1$H NMR (400 MHz, $d_6$-DMSO) δ 9.60 (s, 1H), 7.24 (d, J = 8.4 Hz, 1H), 7.16 (t, J=5.2 Hz, 1H), 4.10-3.95 (m, 4H), 3.95-3.80 (m, 1H), 3.00-2.85 (m, 2 H), 2.58-2.36 (m, 2H), 1.46-1.15 (m, 6H).

Alternatively, di-PEG aldehyde was prepared in the following manner:

The two amino groups of commercial available homo-lysine (Astatech Pharmaceutical Co., Ltd, China) were protected by benzyloxycarbonyl. The N-protected homo-lysine was esterified and reduced to form an aldehyde compound. The aldehyde group was subsequently protected with ethylene glycol. The benzyloxycarbonyl protecting group then was removed by hydrogenation in the presence of a palladium catalyst. The N-deprotected compound was reacted with activated mPEGOH (Sunbio Chemicals Co., Ltd., South Korea) in a mild basic condition. The resulting product was stirred in pH 2.0 citric acid buffer (Sigma-Aldrich, Germany) at 25° C. for 72 hours to remove the aldehyde protecting group. 109 g of di-PEG polymer aldehyde was obtained (yield: 95%). Purity was more than 97.7% (determined by HPLC) and more than 95% (determined by $^1$H NMR analysis).

Preparation of Human rhIFN-β Ser$_{17}$

A DNA fragment encoding human INF-β Ser$_{17}$ was cloned into expression vector pET24a to produce an expression plasmid rhIFN-β Ser$_{17}$-pET24a. This expression plasmid was transformed into *E. coli* and positive transformants, i.e., clones carrying the expression plasmid, were selected, cultivated, and the resultant *E. coli* cultures were stored at −80° C.

10 μl of a stored *E.* coli culture mentioned above were inoculated into 200 ml of a seeding medium consisting of Terrific Broth and glycerol, for about 15 hours at 37° C. and 200 rpm. 150 ml of the *E. coli* culture thus obtained were transferred to 2.5 L culture medium containing glucose (10 g/L), MgSO$_4$.7H$_2$O (0.7 g/L), (NH$_4$)$_2$HPO$_4$ (4 g/L), KH$_2$PO$_4$ (3 g/L), K$_2$HPO$_4$ (6 g/L), citrate (1.7 g/L), Yeast Extract (10 g/L), kanamycin (50 mg/ml), chloramphenicol (50 mg/ml), an antifoaming agent, and trace elements including FeSO$_4$.7H$_2$O (10 mg/L), ZnSO$_4$.7H$_2$O (2.25 mg/L) CuSO$_4$.5H$_2$O (1 mg/L), MnSO$_4$.H$_2$O (0.5 mg/L), H$_3$BO$_3$ (0.3 mg/L), CaCl$_2$.2H$_2$O (2 mg/L), (NH$_4$)$_6$Mo$_7$O$_{24}$ (0.1 mg/L), EDTA (0.84 mg/L), and Cl (50 mg/L), and cultivated at 37° C. When the OD$_{600}$ of the *E. coli* culture reached 120 to 140, IPTG (1 M) was added to the culture to induce expression of rhIFN-β Ser$_{17}$. The induced culture was incubated at 37° C. and 300 rpm for 3 hours. When necessary, a feeding medium containing 800 g/l glucose and 20 g/L MgSO$_4$ was added to the *E. coli* culture during incubation.

The *E. coli* culture obtained as described above was subjected to centrifugation to harvest *E. coli* cells. The cells were resuspended in a PBS buffer (0.1 M Na$_2$HPO$_4$, 0.15 M NaCl) and disrupted in an APV Homogenizer. The homogenized solution thus obtained was centrifuged at 10,000 rpm, 4° C. for 15 min. The precipitates (including inclusion body) were collected, resuspended in PBS, and stirred at room temperature for 20-30 min to form a suspension. NaOH (6 N) was added to the suspension to adjust its pH to 12 to allow dissolution of proteins included in the inclusion body. About 2 minutes later, the pH value of the suspension was adjusted to 7.5 with 6 N HCl. The suspension was then subjected to centrifugation and the supernatant thus formed was collected, its protein concentration being determined using a spectrophotometer. The supernatant was mixed with a refolding buffer (TEA, pH 8.3) and incubated at room temperature without being stirred for 24~48 hours. It was then concentrated and dialyzed, using the TFF system and PLCCC cassette provided by Millipore, Inc. The resultant solution was subjected to ultrafiltration, dialysis, and fractionation with a SPFF Sepharose column. Fractions A9 and A10 thus obtained, containing the recombinant protein rhIFN-β Ser$_{17}$, were further fractionated with another SPFF Sepharose column to enrich the recombination protein (in Fractions A8-A10). These rhIFN-β Ser$_{17}$-containing fractions were further purified by gel filtration (Superdex 75 HR 10/300) to obtain the rhIFN-β Ser$_{17}$ protein (1 mg/ml) having a purity of greater than 90%. The bioactivity of the recombinant protein was >2×10$^7$ IU/mg protein.

Preparation of IFN-β-di-PEG polymer conjugate 18.9 mg rhINF-β Ser$_{17}$ and 1.51 g diPEG aldehyde were suspended in 26 mL of 0.1 M sodium phosphate buffer (pH 5.0). To this solution was added 400 eq. of NaCNBH$_3$ (Acros Organics, Belgium). The reaction mixture was stirred at room temperature for 16 hours and then subjected to dialysis with 25 mM tris-HCl (pH 7.8). The crude product was purified by an ion-exchange column to afford 2 mg of IFN-β-di-PEG polymer.

Preparation of human IFN-β

Transformed *E. coli* BLR (DE3)-RIL cells, carrying the encoding sequence of IFN-β operatively linked to an *E. coli* promoter, were inoculated in 250 mL SYN medium (10 g/L of select soytone, 5 g/L Yeast extract, and 10 g/L NaCl) supplemented with 50 μl/mL kanamycin and 50 μl/mL chloramphenicol. The cells were then cultured at 37° C. in a shaker incubator at 220 rpm overnight (i.e., 16 hours).

250 mL of the overnight culture mentioned above were inoculated into 3.0 L basic medium (10 g/L of Glucose, 0.7 g/L of MgSO$_4$.7H$_2$O, 4 g/L of (NH$_4$)$_2$HPO$_4$, 3 g/L of KH$_2$PO$_4$, 6 g/L of K$_2$HPO$_4$, 2 g/L of Citrate, 10 g/L of Yeast extract and 2 g/L of Isoleucine) supplemented with 10 g/L basic glucose, 0.7 g/L feeding MgSO$_4$, 30 mL feeding trace element (10 g/L of FeSO$_4$.7H$_2$O, 2.25 g/L of ZnSO$_4$.7H$_2$O, 1 g/L of CuSO$_4$.5H$_2$O, 0.5 g/L of MnSO4.H$_2$O, 0.3 g/L of H$_3$BO$_3$, 2 g/L of CaCl$_2$.2H$_2$O, 0.1 g/L of (NH4)$_6$Mo$_7$O$_{24}$, 0.84 g/L of EDTA, 50 ml/L of HCl), 25 μl/mL kanamycin and 25 μl/mL chloramphenicol and cultured in a five liter fermentor (Bioflo 3000; Brunswick Scientation Co., Edison N.J.). During fermentation, the pH of the medium was controlled at pH 7.1 by automated addition of a 37% NH$_4$OH solution. The dissolved oxygen (DO) level was maintained at 30%. The feeding solution (800 g/L of glucose, 20 g/L of MgSO$_4$, 50 μl/mL kanamycin and 50 μl/mL chloramphenicol) was added using a program-controlled pump, which was set to feed when DO level exceeds 40~60. When the cell density (OD$_{600}$) in the fermentation culture reached 180 to 200, 4 mL of 1 M Isopropyl-β-D-1-thiogalactopyranoside (IPTG) was added to the fermentation culture to induce IFN β expression, together with 30 mL of feeding trace elements and 25 g of yeast extract. Cells were harvested 5 hours after IPTG induction by centrifugation.

The cell pellets were suspended in PBS buffer (0.1M sodium phosphate, 0.15M sodium chloride, pH 7.4) at an approximate ratio of 1:3 (wet weight g/mL), disrupted by a microfluidizer, and then centrifuged at 10,000 rpm for 20 min at 4° C. The pellet containing inclusion body (IB) was washed twice with PBS buffer, centrifuged as described above, and suspended in 1 L PBS solution (0.1M sodium phosphate, 0.15M sodium chloride, pH 7.4, 3% zwittergent 3-14, 5 mM DTT). After being stirred for 30 minutes, the suspension was subjected to pH adjustment to 12 with 6.0 M NaOH, while stirring to solubilize the pellet. The pH of the suspension was then adjusted to pH 7.5 with 6 N HCl. Upon centrifugation at 10,000 rpm for 20 min, the supernatant, containing soluble IFN β, was collected.

The soluble INF-β was then subjected to refolding as follows. The supernant mentioned above was diluted in 10 L of a freshly prepared refolding buffer (100 mM Tris-HCl (pH 7.6), 0.5 M L-Arginine, 2 mM EDTA) for form a refolding mixture. The mixture was incubated for 48 hr without stirring. After incubation, the mixture, containing refolded recombinant IFN-β, was dialyzed against 20 mM Tris (with 100 mM NaCl, 0.05% zwittergent 3-14, pH 7.0) buffer.

The dialyzed mixture was loaded onto a SP-Sepharose column (GE Amersham Pharmacia), which was pre-equilibrated and washed with a 20 mM Tris-HCl, 100 mM NaCl buffer (pH 7.0). IFN β was eluted with a solution containing 20 mM Tris-HCl buffer (pH 7.0) and 200 mM NaCl. Fractions containing IFN β was collected based on their absorbance at 280 nm. The IFN β contained therein was further purified by a hydrophobic interaction column (GE healthcare, Butyl Sepharose Fast Flow), which was pre-equilibrated and washed with a solution containing 1.0 M ammonium sulphate, 20 mM sodium acetate and 0.05% zwittergent (pH 4.5). IFN β was eluted using a solution containing 0.5 M ammonium sulphate and 20 mM sodium acetate. Fractions containing the protein were collected based on their absorbance at 280 nm. These fractions were pooled and the concentration of IFN β was determined by BCA protein assay (BCA™ Protein assay, Pierce).

Preparation of PEG-IFN-β conjugate

To a solution of di-PEG aldehyde (296 mg, 7.4 μmol) in water (1.46 mL) was added 2 M sodium phosphate buffer (pH 4.0, 0.37 mL), zwittgen 3-14 (1.48 mL, 10% in water) and INF-β (14.8 mg in 3.7 mL of pH 4.5 buffer containing 20 mM sodium acetate, 0.7% ammonium sulfate and 0.05% detergent). The reaction mixture was stirred at room temperature for 10 minutes, followed by addition of the cyanoborohydride aqueous solution (400 mM, 92.5 μL, 37 μmol). The reaction mixture was stirred in the dark for 40 hours and purified by SP HP Sepharose chromatography. Fractions containing the desired PEG-IFN β conjugate were collected based on their retention time and absorbance at 280 nm. The concentration of the conjugate was determined by BCA protein assay (BCA™ Protein assay, Pierce).

Pharmacokinetic Study in Rats

A pharmacokinetic study was performed in a rat model to compare serum half-life of IFN-β and PEG-IFN-β. Male rats (250~350 gm) were administered intravenously at a dose of 600 μg/kg IFN β (n=3) and PEG-IFN β (n=3). Blood (250 μL) was collected from each rat before administration and at 0.1, 1, 2, 4, 6, 10, 24, 48, 72, and 96 hours after administration. Serum samples were prepared from the blood and the amounts of IFN-β contained in the samples were analyzed by an Enzyme-linked immunoassay (ELISA). The serum half-life of IFN-β and PEG-IFN-β was 2 hours and 20 hours respectively, calculated from the serum concentration of the last three time points.

EXAMPLE 2:

EPO-PEG polymer conjugate

Preparation of PEG-EPO

To a solution of di-PEG aldehyde (267 mg, 6.1 μmol) in water (2.67 mL) was added 2 M sodium phosphate buffer (pH 4.0, 1 mL) and EPO (10 mg in 3.03 mL of pH 7.3 buffer containing 20 mM sodium phosphate and 150 mM NaCl). The reaction mixture was stirred at room temperature for 10 minutes, followed by the addition of the Sodium cyanoborohydride aqueous solution (400 mM, 100 μL, 40 μmol). The reaction mixture was stirred in the dark for 17 hours and purified by a SP Toyopearl column (Tosoh). The column was equilibrated with 20 mM Sodium acetate buffer, pH 4.5. The reaction mixture was diluted to a concentration of 0.3-0.4 mg/ml and loaded onto the SP Toyopearl column. Fractions containing the desired PEG-EPO conjugate were collected based on their retention time and absorbance at 280 nm. The concentration of the conjugate was determined by 280 nm UV absorbance.

Pharmacokinetic Study in Rats

A pharmacokinetic study was performed in a rat model to compare serum half-life of EPO and PEG-EPO. Male rats (250~350 gm) were administered intravenously with EPO (n=5) and PEG-EPO (n=5) at a dose of 25 μg/kg. Blood (250 μL) was drawn from each rat before administration and 0.088, 0.75, 1.5, 3, 6, 10, 24, and 48 hours post administration. For PEG-EPO treated rats, blood samples were further collected at 72 and 96 hours after administration. Serum samples were prepared from the blood and analyzed with an Enzyme-linked immunoassay (ELISA) to determine the amounts of EPO contained therein. The results show that the serum half-life of EPO was 9 hours while that of PEG-EPO was significantly increased, i.e., 38 hours.

Preparation of EPO-PEG polymer conjugate 0.2 mg of EPO (Cashmere Scientific Company, Taiwan) and 4 mg of di-PEG aldehyde (20 equal.) were suspended in 0.1 M phosphate buffer (pH 5.0). To this solution was added 400 eq. of $NaCNBH_3$. The reaction mixture was stirred at room temperature for 16 hours. HPLC confirmed formation of EPO-di-PEG polymer.

EXAMPLE 3

GH—PEG polymer conjugate

Preparation of Met-hGH

Transformed *E. coli* BLR (DE3)-RIL cells, capable of expression Met-hGH, were cultured following the fermentation procedure described above for expression of Met-hGH.

Cells were harvested via centrifugation and cell pellet was suspended in TE buffer (50 mM Tris-HCl, 1 mM EDTA, pH 8.0) at an approximate ratio of 1:3 (wet weight g/mL). The cells were then disrupted by a microfluidizer and then centrifuged at 10,000 rpm for 20 min. The pellet containing inclusion body (IB) was washed twice with TED buffer (50 mM Tris-HCl, 1 mM EDTA, 2% Deoxycholate, pH 8.0), centrifuged as described above, and suspended in MilliQ water and centrifuged at 20,000 rpm for 15 min. The IBs were suspended in 400 mL of 50 mM TUD solution (50 mM Tris-HCl, 4 M Urea, 2.5 mM DTT, pH 10.0) and the suspension was centrifuged at 20,000 rpm for 20 min; supernatant collected.

The supernatant was diluted in 2.0 L of a freshly prepared refolding buffer (50 mM Tris-HCl, 0.5 mM EDTA, 5% glycerol 10 mM GSH/1 mM GSSG, pH 8.0). The mixture thus formed was incubated for 36hr without stirring and then dialyzed against 20 mM Tris buffer (pH 7.0).

The dialyzed mixture, containing Met-hGH, was loaded onto a Q-Sepharose column (GE Amersham Pharmacia, Pittsburgh, Pa.), which was pre-equilibrated and washed with a 20 mM Tris-HCl buffer, pH 7.0. Met-hGH was eluted a solution containing 20 mM Tris-HCl buffer, pH 7.0 and 100 mM NaCl. Fractions containing Met-hGH, determined by their absorbance at 280 nm, were collected, pooled, and loaded onto a hydrophobic interaction column (GE Amersham Pharmacia, Pittsburgh, Pa.), pre-equilibrated and washed with a 20 mM sodium acetate buffer (pH 7.0), at a flow rate of 5 ml/min. Met-hGH was eluted with a solution containing 20 mM sodium acetate buffer and 150 mM ammonium sulfate. A fraction containing Met-hGH was collected and subjected to BCA protein assay (BCA™ Protein assay, Pierce) to determine the Met-hGH concentration.

Preparation of PEG-Met-hGH conjugate

To a solution of di-PEG aldehyde (74 mg, 1.7 μmol) in water (387 μL) was added 2 M sodium phosphate buffer (pH 4.0, 374 μL) and human GH (22.4 mg in 6.5 mL of pH 4.5 buffer containing 20 mM sodium acetate and 150 mM NaCl). The reaction mixture was stirred at room temperature for 10 minutes, followed by the addition of the sodium cyanoborohydride aqueous solution (400 mM, 140 μL, 56 μmol). The reaction mixture was stirred in the dark for 17 hours and purified by SP XL Sepharose chromatography. Fractions containing the desired polymer-protein conjugate were collected based on their retention time and absorbance at 280 nm. The concentration of conjugate was determined by a protein assay kit using the Bradford method (Pierce, Rockford, Ill.).

Pharmacokinetic Study in Rats

A pharmacokinetic study was performed in a rat model to compare serum half-life of Met-hGH and PEG-Met-hGH. Male rats (250~350 gm) were administered intravenously with Met-hGH (n=5) or PEG-Met-hGH (n=5) at a dose of 100 μg/kg. Blood samples were collected from Met-hGH-treated rats before administration and 0.083, 1, 2, 4, 8, 12, and 24 hours after administration; and were collected from PEG-Met-hGH-treated rats before administration and 0.33, 1, 4, 8, 12, 24, 48, 72, and 96 hours after administration. Serum samples were prepared from the blood and analyzed with an Enzyme-linked immunoassay (ELISA) to determine hGH concentrations. The serum half-life of Met-hGH and PEG-Met-hGH was 3 hours and 35 hours respectively.

Other Embodiments

All of the features disclosed in this specification may be combined in any combination. Each feature disclosed in this specification may be replaced by an alternative feature serving the same, equivalent, or similar purpose. Thus, unless expressly stated otherwise, each feature disclosed is only an example of a generic series of equivalent or similar features.

From the above description, one skilled in the art can easily ascertain the essential characteristics of the present invention, and without departing from the spirit and scope thereof, can make various changes and modifications of the invention to adapt it to various usages and conditions. Thus, other embodiments are also within the scope of the following claims.

What is claimed is:

1. A peptide-polymer conjugate of the following formula:

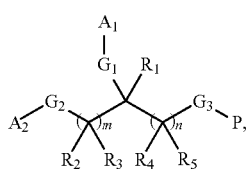

wherein
each of $R_1$, $R_2$, $R_3$, $R_4$, and $R_5$, independently, is H, $C_{1-10}$ alkyl, $C_{2-10}$ alkenyl, $C_{2-10}$ alkynyl, aryl, heteraryl, $C_{3-8}$ cycloalkyl, or $C_{3-8}$ heterocycloalkyl;
each of $A_1$ and $A_2$, independently, is a polymer;
each of $G_1$, $G_2$, and $G_3$, independently, is a bond or a linking functional group;
P is selected from the group consisting of an interferon-β, an erythropoietin, and a growth hormone, the nitrogen atom of the N-terminus of P being bonded to $G_3$;
m is 0 or an integer of 1-10; and
n is an integer of 1-10.

2. The conjugate of claim 1, wherein P is interferon-β.
3. The conjugate of claim 2, wherein P is rINF-β $Ser_{17}$.
4. The conjugate of claim 2, wherein P is modified interferon-β containing 1-4 additional amino acid residues at the N-terminus.
5. The conjugate of claim 1, wherein P is erythropoietin.
6. The conjugate of claim 1, wherein each of $A_1$ and $A_2$ is a polyethylene glycol having a molecular weight of 2-100 kD.
7. The conjugate of claim 6, wherein each of $A_1$ and $A_2$ is a polyethylene glycol having a molecular weight of 10-30 kD.
8. The conjugate of claim 7, wherein each of $G_1$ and $G_2$ is

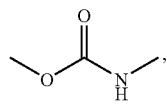

in which the O is bonded to $A_1$ or $A_2$, and the N atom is bonded to a carbon atom; and $G_3$ is a bond.

9. The conjugate of claim 8, wherein m is 4, n is 2, and each of $R_1$, $R_2$, $R_3$, $R_4$, and $R_5$ is H.
10. The conjugate of claim 9, wherein P is interferon-β.
11. The conjugate of claim 10, wherein P is rINF-β $Ser_{17}$.
12. The conjugate of claim 10, wherein P is modified interferon-β containing 1-4 additional amino acid residues at the N-terminus.
13. The conjugate of claim 9, wherein P is erythropoietin.
14. The conjugate of claim 9, wherein P is growth hormone.
15. The conjugate of claim 1, wherein P is growth hormone.
16. The conjugate of claim 1, wherein the conjugate is

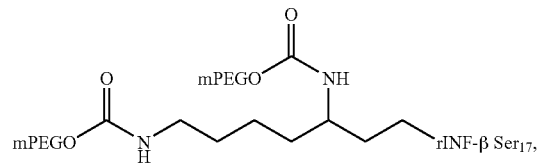

in which mPEG is methoxy-capped polyethylene glycol having a molecular weight of 20 kD.

17. The conjugate of claim 1, wherein the conjugate is

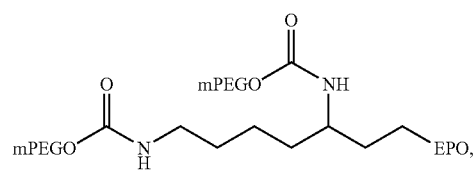

in which mPEG is methoxy-capped polyethylene glycol having a molecular weight of 20 kD.

18. The conjugate of claim 1, wherein the conjugate is

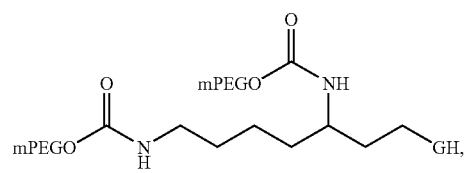

in which mPEG is methoxy-capped polyethylene glycol having a molecular weight of 20 kD.

* * * * *